US006865196B2

(12) United States Patent
Dobbs et al.

(10) Patent No.: US 6,865,196 B2
(45) Date of Patent: Mar. 8, 2005

(54) LASER SPECTROSCOPY USING A MASTER/SLAVE ARCHITECTURE

(75) Inventors: Michael E. Dobbs, Fort Wayne, IN (US); Peter Wheel, Fort Wayne, IN (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 311 days.

(21) Appl. No.: 10/155,172

(22) Filed: May 28, 2002

(65) Prior Publication Data

US 2003/0227629 A1 Dec. 11, 2003

(51) Int. Cl.[7] .............................................. H01S 3/10
(52) U.S. Cl. ........................... 372/20; 372/32; 372/43; 372/44; 372/45; 372/46; 372/47; 372/48; 372/49; 372/50; 356/5; 356/28.5; 356/345; 356/349; 356/351
(58) Field of Search ...................... 372/20, 32, 43–50; 356/5, 28.5, 345, 349, 351

(56) References Cited

U.S. PATENT DOCUMENTS

| | | | |
|---|---|---|---|
| 4,817,100 A | 3/1989 | Cameron et al. | 372/32 |
| 4,817,101 A | 3/1989 | Wyeth et al. | 372/32 |
| 4,856,899 A * | 8/1989 | Iwaoka et al. | 356/454 |
| 4,948,251 A | 8/1990 | Kondo | 356/349 |
| 5,018,151 A | 5/1991 | Seaton | 372/18 |
| 5,022,757 A | 6/1991 | Modell | 356/318 |
| 5,272,513 A | 12/1993 | Vahala et al. | 356/28.5 |
| 5,504,719 A * | 4/1996 | Jacobs | 367/149 |
| 5,544,183 A | 8/1996 | Takeda | 372/38 |
| 5,742,399 A | 4/1998 | McAndrew et al. | 356/437 |
| 5,861,975 A | 1/1999 | Sakuyama et al. | 359/187 |
| 6,327,039 B1 * | 12/2001 | de Groot et al. | 356/517 |
| 2004/0017833 A1 * | 1/2004 | Cundiff et al. | 372/18 |

* cited by examiner

*Primary Examiner*—Minsun Oh Harvey
*Assistant Examiner*—Delma R. Flores Ruiz
(74) *Attorney, Agent, or Firm*—RatnerPrestia

(57) ABSTRACT

A system for tuning one or more second radiant sources relative to a first radiant source may include a coupler configured to combine output signals from the first radiant source and a second radiant source to generate a heterodyne signal containing a frequency difference between the output signals from the first radiant source and the second radiant source. A photodetector may be configured to convert the heterodyne signal into an electrical signal containing the frequency difference. A spectrum analyzer may be configured to measure the frequency difference in the electrical signal and generate a precise difference value. A controller may be configured to adjust a wavelength of the second radiant source relative to that of the first radiant source based on the precise difference value. Laser spectroscopy may be performed by passing the output signals from the first radiant source and the second radiant source through a sample volume and detecting reflected or emitted radiation.

15 Claims, 6 Drawing Sheets

| TABLE ENTRIES 405 | SPECTRAL FEATURE 410 | NOMINAL OFFSET SLAVE 1 415-1 | ... | NOMINAL OFFSET SLAVE n 415-n | MEASURED $f_{DIFF}$ SLAVE 1 420-1 | ... | MEASURED $f_{DIFF}$ SLAVE n 420-n | $\Delta f$ SLAVE 1 425-1 | ... | $\Delta f$ SLAVE n 425-n |
|---|---|---|---|---|---|---|---|---|---|---|
| → | $f_{REF1}$ | $f1_{OFFSET}$ | | $fN_{OFFSET}$ | $f_{DIFF1}$ | | $f_{DIFFN}$ | $\Delta f_1$ | | $\Delta f_N$ |
| → | $f_{REF2}$ | $f1_{OFFSET}$ | | $fN_{OFFSET}$ | $f_{DIFF1}$ | | $f_{DIFFN}$ | $\Delta f_1$ | | $\Delta f_N$ |
| → | $f_{REF3}$ | $f1_{OFFSET}$ | | $fN_{OFFSET}$ | $f_{DIFF1}$ | | $f_{DIFFN}$ | $\Delta f_1$ | | $\Delta f_N$ |

SPECTROSCOPIC DATA TABLE 305

LASER SPECTROSCOPY USING A MASTER/SLAVE ARCHITECTURE

FIELD OF THE INVENTION

The present invention relates generally to laser spectroscopy and, more particularly, to systems and methods for generating precisely known wavelengths for laser spectroscopy.

BACKGROUND OF THE INVENTION

In tunable diode laser absorption spectroscopy (TDLAS), a single wavelength emitted by a tunable diode laser may be used as a source to measure the absorption spectra of a material under test. Tunable lasers may be "locked" to the center of a spectral feature of interest by passing the optical signal from the tunable laser through a "sample volume" containing the material and measuring the differential absorption with a detector. The sample volume may be, for example, a cell in a laboratory or a volume in the atmosphere. By modulating the wavelength of the tunable laser, measuring the response, and computing one or more derivatives, the tunable laser may be precisely "line-locked" to the center of the desired absorption feature.

Determination of the concentration of the material under test generally requires accurate knowledge of temperature and pressure, and absorption measurements of the material under test as a function of wavelength. In many cases, it is necessary to measure the absorption at more than one wavelength to accurately determine the concentration of the material under test. Although "line-locking" techniques may precisely lock to a desired spectral feature, these techniques do not readily permit precise measurements, for example, along a side of the desired spectral feature or of another nearby spectral feature. Without such measurements, precision spectroscopy and determination of a material's concentration may not be possible.

Therefore, there exists a need for mechanisms in a laser spectroscopy system that enable the generation of at least one precisely known wavelength for determining the concentration of a material under test.

SUMMARY OF THE INVENTION

Systems and methods consistent with the present invention address this need and others by using a spectrum analyzer to precisely measure an electrical signal obtained from a heterodyne signal from two laser sources. The spectrum analyzer enables precise measurement of frequency differences in the electrical signal, which may be used to precisely tune one laser source relative to the other. Such precisely tuned sources may be used for laser spectroscopy of a sample volume.

In accordance with one purpose of the invention as embodied and broadly described herein, a method may include generating a heterodyne optical signal from two optical sources and measuring the heterodyne optical signal with a precision greater than 100 MHz to obtain a precise measurement value. One of the optical sources may be adjusted using the precise measurement value.

In another implementation consistent with the present invention, a method may include setting a first laser to output a first signal at a first wavelength and combining the first signal and a second signal from a second laser to form a combined optical signal. The combined optical signal may be converted to a combined electrical signal. The combined electrical signal may be measured to produce a precise measured value. A second wavelength of the second signal may be adjusted relative to the first wavelength using the precise measured value.

In a further implementation consistent with the present invention, a system for tuning one or more second radiant sources relative to a first radiant source may include a coupler configured to combine output signals from the first radiant source and a second radiant source to generate a heterodyne signal containing a frequency difference between the output signals from the first radiant source and the second radiant source. A photodetector may be configured to convert the heterodyne signal into an electrical signal containing the frequency difference. A spectrum analyzer may be configured to measure the frequency difference in the electrical signal and generate a precise difference value. A controller may be configured to adjust a wavelength of the second radiant source relative to that of the first radiant source based on the precise difference value.

In yet another implementation consistent with the present invention, a system for tuning a second laser relative to a first laser may include a detector configured to produce an offset signal corresponding to a frequency difference between outputs of the first laser and the second laser. A spectrum analyzer may be configured to measure a frequency of the offset signal and generate a precise measurement value. A controller may be configured to tune the output of the second laser relative to the output of the first laser using the precise measurement value.

BRIEF DESCRIPTION OF THE DRAWINGS

The accompanying drawings, which are incorporated in and constitute a part of this specification, illustrate an embodiment of the invention and, together with the description, explain the invention. In the drawings.

FIG. 4 illustrates an exemplary spectroscopic data table stored in the database of FIG. 3 consistent with the present invention;

DETAILED DESCRIPTION

The following detailed description of the invention refers to the accompanying drawings. The same reference numbers in different drawings identify the same or similar elements. Also, the following detailed description does not limit the invention. Instead, the scope of the invention is defined by the appended claims.

Systems and methods consistent with the present invention may provide mechanisms for slaving one or more lasers to a master laser using heterodyned difference signal outputs from a photodetector. The photo-detector output may include a frequency difference between a respective slaved laser and the master laser that, when measured by a spectrum analyzer, may be used to adjust the frequency of the output signal from the slave laser to a precise value.

EXEMPLARY LASER SPECTROSCOPY SYSTEM

Figure 1:
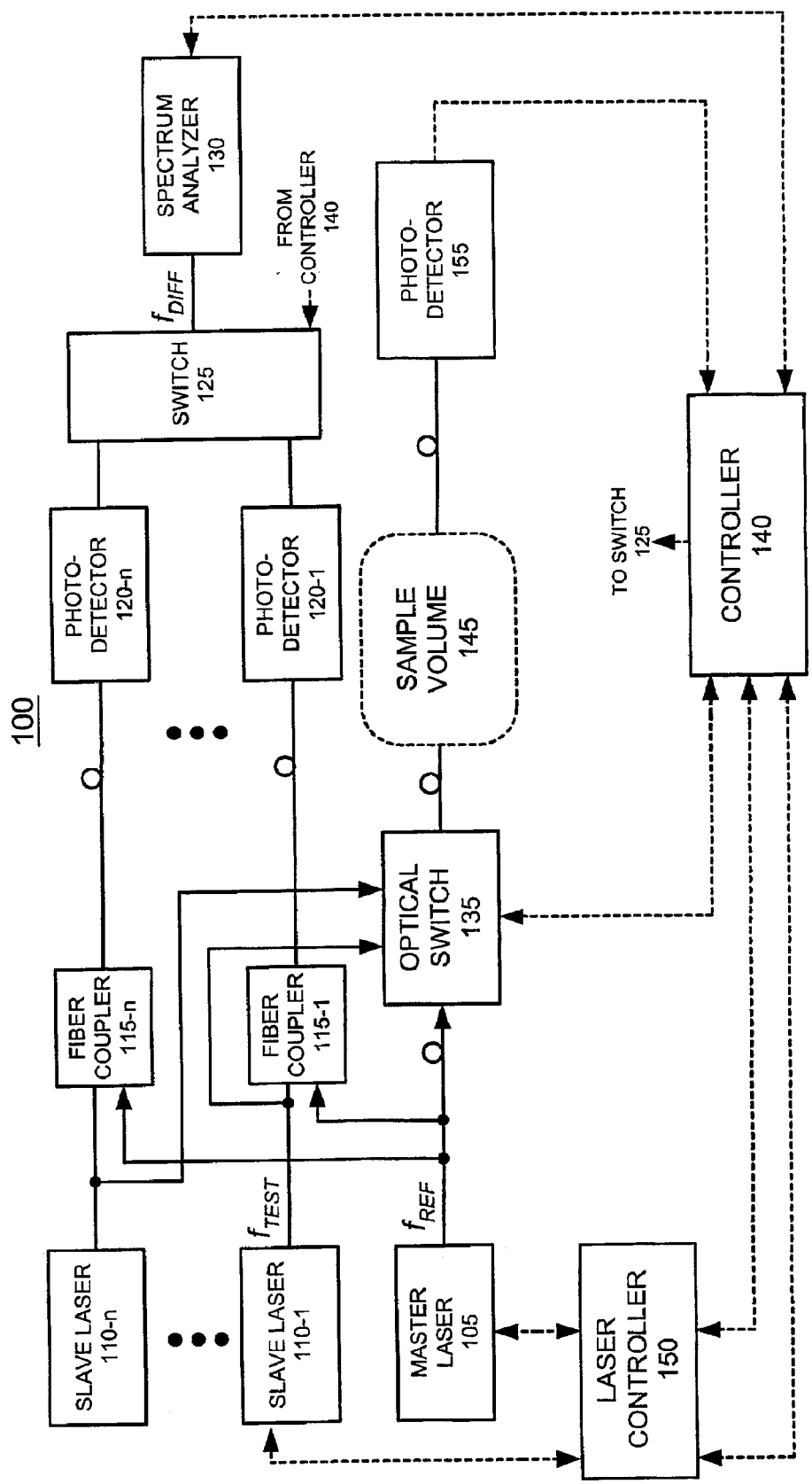
FIG. 1 illustrates an exemplary laser spectroscopy system consistent with the present invention.

FIG. 1 illustrates an exemplary laser spectroscopy system 100 consistent with the present invention. System 100 may include a master laser 105, one or more slave lasers 110-1 to 110-*n*, one or more fiber couplers 115-1 to 115-*n*, one or more photodetectors 120-1 to 120-*n*, an electrical switch 125, a spectrum analyzer 130, an optical switch 135, a controller 140, a sample volume 145, a laser controller 150, and an absorption photodetector 155.

The master laser 105 may include a tunable laser that is controlled by a control signal. Depending on the control signal, the master laser may emit any number of reference frequencies $f_{REF}$. The master laser 105 may include, for example, a distributed feedback (DFB) laser that is precisely tunable in frequency/wavelength via a combination of temperature and current. Examples of such tunable lasers include gas, solid, diode, and other types of lasers.

Similarly, the slave lasers 110-1 to 110-*n* (only one of which will be discussed for purposes of illustration) each may include a tunable laser that is controlled by a separate control signal than the control signal for the master laser 105. Depending on the control signal, the slave laser 110-1 may emit any number of test frequencies $f_{TEST}$. The slave laser 110-1 also may include, for example, a distributed feedback (DFB) laser that is precisely tunable in frequency/wavelength via a combination of temperature and current.

Fiber couplers 115-1 to 115-*n* may be configured to combine their respective input signals into respective single output signals. In the configuration of FIG. 1, the output signals from the master laser 105 and the slave laser 110-1 are combined by fiber coupler 115-1, for example, to generate a heterodyne laser signal at the output of fiber coupler 115-1. Such a heterodyne signal may have a difference component in the microwave range (e.g., 1–20 GHz). Other fiber couplers 115-2 to 115-*n*, if present, may be configured to combine the output signal from the master laser 105 with a respective slave laser 110-2 to 110-*n* in a manner similar to that described above with respect to fiber coupler 115-1.

In one implementation consistent with the principles of the invention, at least one fiber coupler 115-*n* may be modified, for example, by the addition of an optical switch, to permit the heterodyning of two slave lasers 110. Such an arrangement may facilitate adjusting a first slave laser (e.g., 110-1) relative to the master laser 105, and then adjusting a second slave laser (e.g., 110-2) relative to the first slave laser. Although named a "fiber coupler," those skilled in the art will appreciate that couplers 115 may include any type of optical couplers, and are not necessarily limited to fiber optic-related couplers.

Photodetectors 120-1 to 120-*n* may be configured to convert one or more heterodyne optical signals from the fiber couplers 115-2 to 115-*n* into corresponding electrical signals. Photodetectors 120-1 to 120-*n* may include, for example, high speed (i.e., high bandwidth) photodiodes. In practice, an optical heterodyne signal will contain both the sum and difference of the frequencies of its respective components (i.e., signals from the master and a slave laser). Photodetectors 120-1 to 120-*n* may detect the difference frequency $f_{DIFF}$, because the sum frequency may be above the operating frequency range of the photodetectors.

Switch 125 may select among the electrical output signals from photodetectors 120-1 to 120-*n* based on a switch control signal. Switch 125 may output one or more selected electrical signals at frequency $f_{DIFF}$. In another implementation consistent with the principles of the invention, the combination of the photodetectors 120 and the switch 125 may be replaced with an n-to-1 optical switch and a single photodetector. Such an alternate implementation would also accomplish the conversion of an optical signal from a selected fiber coupler 115 to an electrical signal at frequency $f_{DIFF}$.

Spectrum analyzer 130 may receive the electrical signal from the switch 125, and may precisely measure its frequency $f_{DIFF}$. Spectrum analyzer 130 may include, for example, an Agilent® 85835 or a similar type of spectrum analyzer. Such spectrum analyzers may achieve precision in their measurements of up to one part in $10^9$ (e.g., 1 Hz per GHz).

The use of a spectrum analyzer (or similar instrument) to precisely measure an electrical signal obtained from an optical signal may provide, for example, on the order of one thousand times more precision than measuring the optical signal directly with a wavemeter. As an example, the resolution of a wavemeter at 1.5 $\mu$m may be 0.5 pm. By contrast, the resolution of a spectrum analyzer at the same wavelength may be 1 MHz to 1 kHz, which equate to 0.008 to 0.000008 pm. Hence, measurement with the spectrum analyzer 130 as shown in FIG. 1 permits determining $f_{DIFF}$ much more precisely than with optical measurement techniques, which in turn enables more precise adjustment (i.e., "finer" tuning) of, for example, slave lasers 110-1 to 110-*n*.

Optical switch 135 may select among the output signal of the master laser 105 and one or more output signals from slave lasers 110-1 through 110-*n*. Optical switch 135 may be controlled by a control signal that determines which among the output signals from slave lasers 110-1 through 110-*n* and the output signal of the master laser 105 are selected and output by the switch. The optical signal output by the optical switch 135 is transmitted through a sample volume 145.

Sample volume 145 may include a material to be examined by laser absorption spectroscopy. In one implementation, the sample volume 145 may include a cell in, for example, a laboratory environment. In other implementations, the sample volume 145 may include a volume of the atmosphere, which may or may not have a scattering background (e.g., the ground, for a down-looking system 100). Sample volume 145 may contain a substance having at least one absorption/reflection feature to which master laser 105 may be locked.

Photodetector 155 may detect optical radiation reflected from or transmitted through the sample volume 145. Photodetector 155 may be configured to convert received optical energy into an electrical signal, which may either be calibrated to correspond to the optical energy by the photodetector 155 or by later processing.

Laser controller 150 may be configured to control the master laser 105 and one or more slave lasers 110-1 to 110-*n*. Laser controller 150 may effect such control, for example, by varying current that drives the master and slave lasers 105 and 110. In turn, the laser controller 150 may receive feedback signals from these lasers to aid in their control. The laser controller 150 may control the master laser 105 and one or more slave lasers 110-1 to 110-*n* based on input control signals that it receives.

Controller 140 may receive input signals from the photodetector 155 and the spectrum analyzer 130, and may be configured to generate control signals for the laser controller 150, the switch 125, and the optical switch 135 based on the input signals. Controller 140 may be configured to command laser controller 150 to adjust, using conventional mechanisms, the wavelength/frequency of master laser 105 and/or slave lasers 110. Controller 140 may also be configured to lock master laser 105 onto a certain spectral feature, and may include circuitry (e.g., phase locked loop, etc.) to facilitate locking one laser on a particular spectral peak or feature.

In one implementation consistent with the principles of the invention, a control volume or cell (not shown) may be present in the system 100, which may provide the master laser 105 with a controlled sample on which to lock. For example, it may be desirable to optimize the control cell's path length, gas composition, pressure, and temperature for the purpose of accurately locking in the master laser 105 to a particular feature. For example, a gas in the control cell may have 100% concentration, but a low pressure to minimize pressure broadening.

If the control cell (not shown) is not present in system 100, however, the signal from the master laser 105 may be sent through the sample volume 145 by the optical switch 135. Once the master laser 105 has been locked to a spectral feature of the material in the sample volume 145, the optical switch 135 may be used to send one or more output signals from the slave lasers 110-1 to 110-$n$, sequentially.

Exemplary Controller

Figure 2:
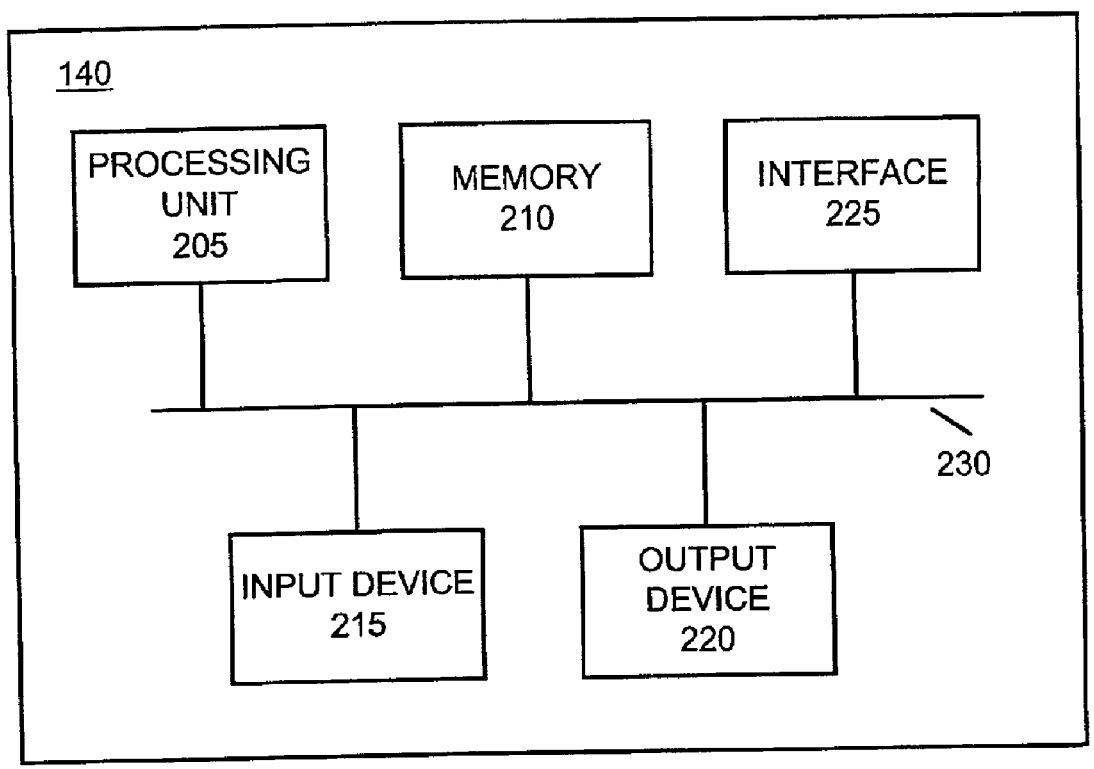
FIG. 2 illustrates an exemplary controller consistent with the present invention.

FIG. 2 illustrates one exemplary embodiment, consistent with the present invention, in which controller 140 may be implemented as a computer. FIG. 2 illustrates exemplary components of such a computer consistent with the invention. In such an implementation, controller 140 may include a processing unit 205, a memory 210, an input device(s) 215, an output device(s) 220, an interface(s) 225, and a bus 230.

Processing unit 205 may perform all data processing functions for inputting, outputting, and processing of data. Memory 210 may include Random Access Memory (RAM) that provides temporary working storage of data and instructions for use by processing unit 205 in performing processing functions. Memory 210 may additionally include Read Only Memory (ROM) that provides permanent or semi-permanent storage of data and instructions for use by processing unit 205. Memory 210 can also include large-capacity storage devices, such as a magnetic and/or optical device.

Input device(s) 215 permits entry of data into controller 140 and may include a user interface (not shown) such as, for example, a keyboard or mouse. Output device(s) 220 permits the output of data in video, audio, or hard copy format. Interface(s) 225 interconnects controller 140 with other devices of system 100, such as, for example, spectrum analyzer 130 and laser controller 150. Bus 230 interconnects the various components of controller 140 to permit the components to communicate with one another.

Exemplary Database

Figure 3:
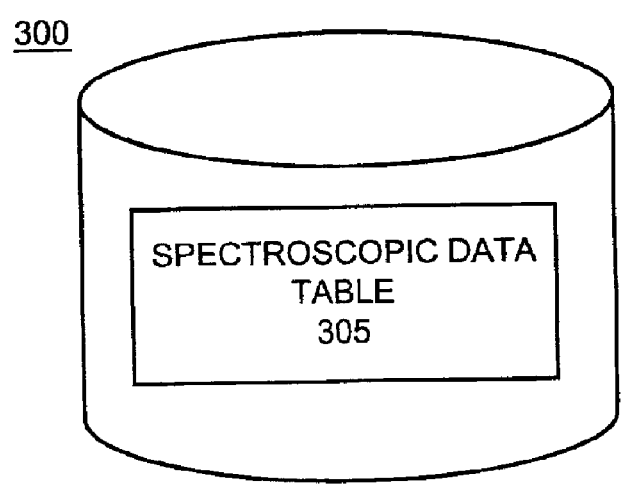
FIG. 3 illustrates an exemplary database associated with the computer of FIG. 2 consistent with the present invention.

FIG. 3 illustrates an exemplary database 300 that may be associated with memory 210 of controller 140. Database 300 may be stored in, for example, memory 210 or may be located external to controller 140. Database 300 may include a spectroscopic data table 305 that contains relevant data for tuning the frequency/wavelength of one or more slave lasers 110 relative to master laser 105.

FIG. 4 illustrates an exemplary spectroscopic data table 305 consistent with the present invention. Spectroscopic data table 305 may include multiple table entries 405, each of which may include a spectral feature 410, a nominal offset value 415 ($f_{OFFSET}$) corresponding to each slave laser, a measured frequency difference value 420 ($f_{DIFF}$) corresponding to each slave laser, and a calculated delta frequency value 425 ($\Delta f$) corresponding to each slave laser. Spectral feature 410 may include a wavelength/frequency ($f_{REF}$) associated with a spectral absorption feature to which master laser 105 may be locked. Each slave nominal offset value 415 ($f_{OFFSET}$) may include a nominal value for an offset of the wavelength/frequency of a respective slave laser 110 from the wavelength/frequency of master laser 105. Each slave frequency difference value 420 ($f_{DIFF}$) may include the actual measured frequency of the heterodyned output signal from photo-detector 120 corresponding to a respective slave laser 110. Delta frequency value 425 ($\Delta f$) may include the difference between the measured slave frequency difference value 420 ($f_{DIFF}$) and the slave nominal offset frequency value 415 ($f_{OFFSET}$) for each respective slave laser 110.

Exemplary Laser Control Process

Figure 5:
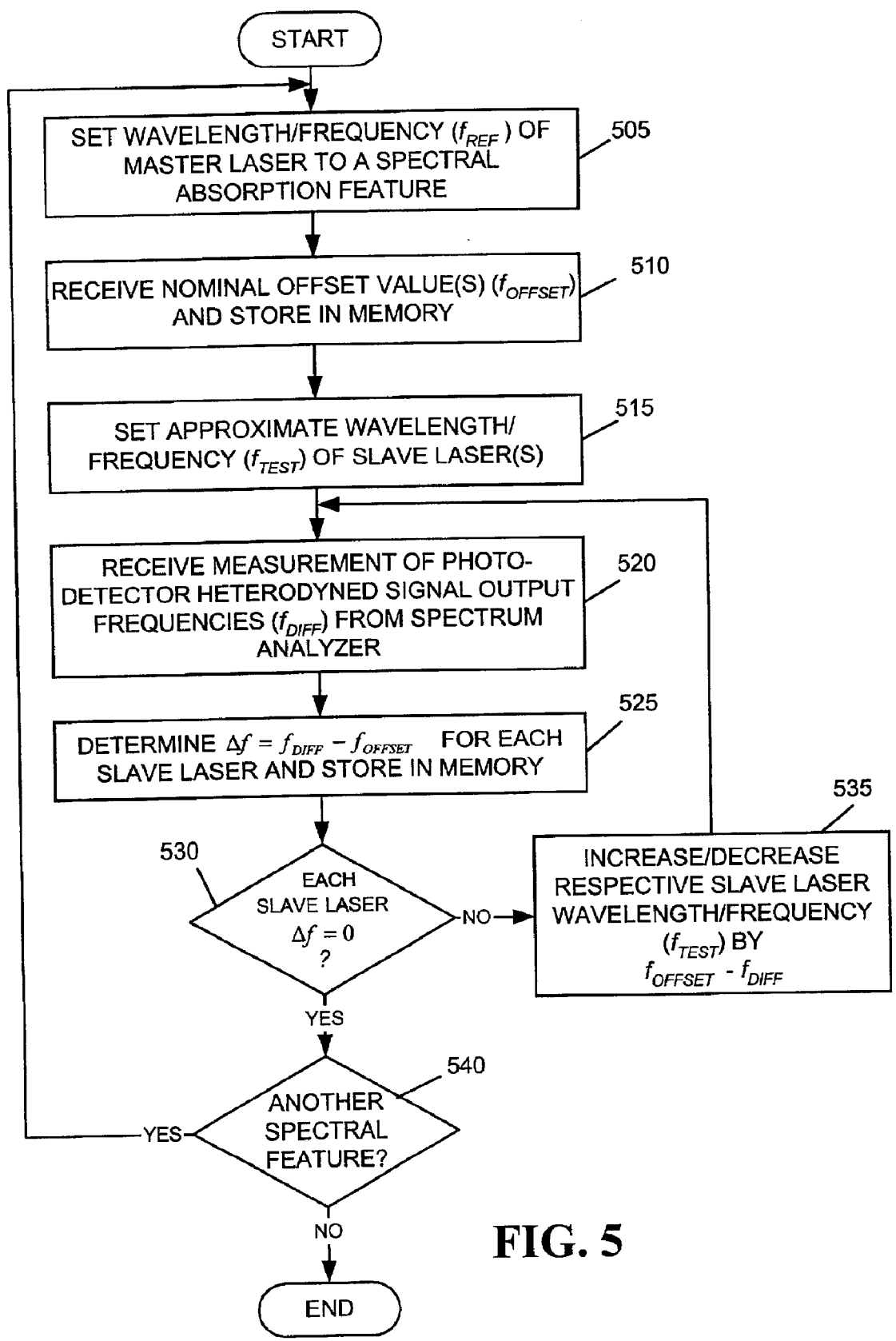
FIG. 5 is a flowchart that illustrates an exemplary laser control process consistent with the present invention.

FIG. 5 is a flowchart that illustrates an exemplary process, consistent with the present invention, for controlling and calibrating the wavelength/frequency of one or more slave lasers 110. As one skilled in the art will appreciate, the method exemplified by FIG. 5 can be implemented as a sequence of instructions and stored in memory 210 of controller 140 for execution by processing unit 205. In other exemplary embodiments, in which controller 140 may be implemented as logic circuitry, one skilled in the art will further appreciate that the method exemplified by FIG. 5 may be implemented using various techniques of logic circuitry construction.

The exemplary process may begin with controller 140 setting the wavelength/frequency ($f_{REF}$) of master laser 105 to a spectral feature 410 of a substance within absorption cell 145 (or the control cell (not shown)) using laser controller 150 [act 505]. The desired spectral feature may be stored, for example, in a corresponding entry 405 of data table 305. The wavelength/frequency ($f_{REF}$) of master laser 105 may be locked to an absorption spectral feature using, for example, several known line-locking techniques.

One such line-locking technique involves passing the output signal from a tunable laser (e.g., master laser 105) through a sample (e.g., sample volume 145 or a control cell) and measuring a differential absorption with a detector (e.g., photodetector 155). An absorption feature or "line" may be located, and the wavelength of the tunable laser may be modulated to either side of the feature's/line's center and a response measured. By computing a first or higher order derivative of the measured signals, the tunable laser (e.g., master laser 105) may be precisely "locked" to the center of the spectral feature or line.

Controller 140 may receive one or more nominal offset values 415 ($f_{OFFSET}$), corresponding to each slave laser 110, from, for example, input device 215, and may store the nominal offset values $f_{OFFSET}$ 415 in data table 305 [act 510]. Controller 140 may then set an approximate wavelength/frequency ($f_{TEST}$) of each slave laser 110 using laser controller 150 [act 515]. $f_{TEST}$ may approximately equal $f_{REF}$ plus $f_{OFFSET}$ for each respective slave laser 110-1 through 110-$n$. Controller 140 may receive, from spectrum analyzer 130, measurements of the frequency ($f_{DIFF}$) of photo-detector 120's signal output(s) [act 520]. The signal output(s) from photo-detector 120 may include the output signal from master laser 105 and a respective slave laser 110 heterodyned as a difference signal representing a frequency difference between the master laser 105 and the respective slave laser 110.

Controller 140 may determine a delta frequency value 425 (Δf) for each slave laser that represents the difference between the measured frequency difference ($f_{DIFF}$) 420 and the nominal offset value ($f_{OFFSET}$) 415 corresponding to each slave laser 110 [act 525]. Each determined delta frequency value Δf 425 may be stored in data table 305. Controller 140 may determine if each slave delta frequency value Δf 425 is equal to zero, indicating that the corresponding measured slave frequency difference ($f_{DIFF}$) 420 is equal to the corresponding slave nominal offset value ($f_{OFFSET}$) 415 [act 530]. If not, controller 140 may, using laser controller 150, increase/decrease the wavelength/frequency ($f_{TEST}$) of each slave laser 110 by an amount equal to each respective difference between $f_{OFFSET}$ and $f_{DIFF}$ ($f_{OFFSET}-f_{DIFF}$) [act 535], and the process may continue at act 520. If the delta frequency value Δf 425 of a respective slave laser 110 is equal to zero, controller 140 may determine if another spectral absorption feature of the substance in absorption cell 145 is to be used [act 540]. If so, the process may return to act 505. If no other spectral features are to be tested, the exemplary process may complete.

Figure 6:
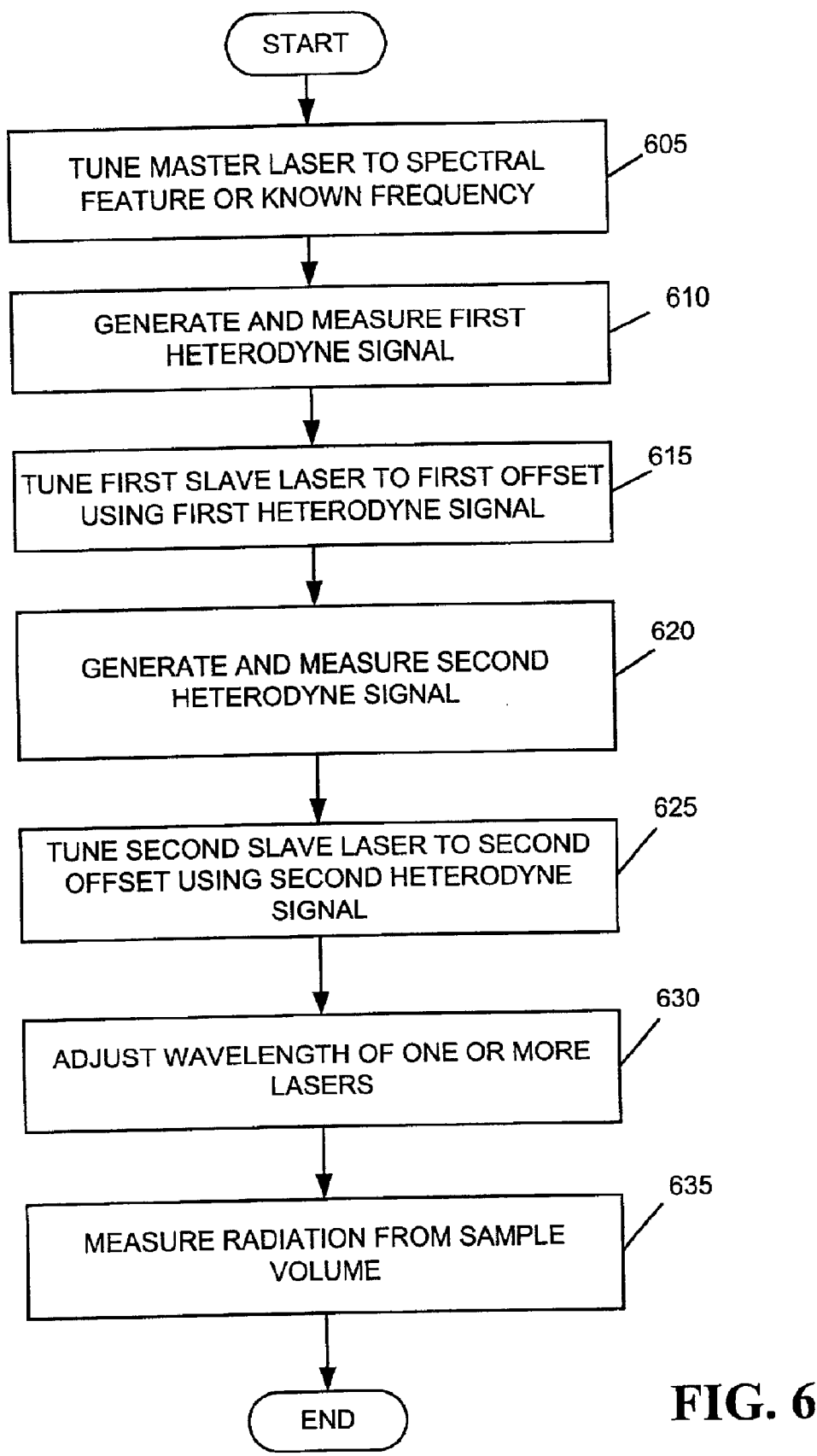
FIG. 6 is a flowchart that illustrates exemplary measurement processing consistent with the principles of the present invention.

FIG. 6 is a flowchart that illustrates exemplary measurement methodology consistent with the principles of the present invention. From FIGS. 1 and 5 above, those skilled in the art will appreciate how slave lasers 110 may be precisely adjusted relative to a master laser 105 using, for example, the spectrum analyzer 130. FIG. 6 describes several measurement techniques that may be employed to perform laser absorption spectroscopy on the sample volume 145.

Processing may begin by tuning the master laser 105 to a spectral feature or a known frequency [act 605]. The master laser 105 may be, for example, "locked in" to a spectral feature using the derivative techniques described above. In another implementation consistent with the principles of the invention, the master laser 105 may be tuned to a known reference wavelength/frequency, possibly using the spectrum analyzer 130.

Processing may continue with the generation and measurement of a first heterodyne signal [act 610]. In one implementation, a coupler 115 may combine output signals from the master laser 105 and a first slave laser (e.g., slave laser 110-1) to form the first heterodyne signal. Other ways of forming such a heterodyne signal are possible. High speed photodetector 120-1 may convert the heterodyne optical signal into an electrical signal, which may be measured down to a precision of 1 MHz or less by the spectrum analyzer 130. By contrast, a wavemeter (an optical measurement device), if used instead of the photodetector 120-1 and spectrum analyzer 130, may only achieve a maximum precision of around 10 GHz. Hence, measurement using a spectrum analyzer 130 or other precise instrument consistent with the principles of the invention may achieve much higher precision (i.e., more significant digits). This, in turn, enables much finer (i.e., more precise) control of the slave lasers 110-1 to 110-n.

The first slave laser 110-1 may be tuned to a first offset in wavelength/frequency from the master laser 105 [act 615]. Because such tuning is based on the precisely measured first heterodyne value from the spectrum analyzer 130, the first slave laser 110-1 may be controlled in frequency steps down to 1 MHz or so. In practice, the spectrum analyzer 130 may produce precision down to about 1 kHz (e.g., measurement precisions on the order of 100 kHz, 10 kHz, and 1 kHz), but wavelength drift or jitter of the first slave laser 110-1 may limit the precision with which its wavelength may be controlled to about 1 MHz. Because a precision of around 1 MHz is possible, the first slave laser may also be tuned to with lower precision (e.g., in increments on the order of 10 MHz, 100 MHz, or 1 GHz).

The first slave laser 110-1 may be tuned, assuming that the spectral feature to which the master laser 105 is locked has sloping sides, to a value along the side of the feature. Alternately, the first slave laser 110-1 may be tuned to an adjacent spectral feature that is a known distance from the spectral feature to which the master laser 105 is locked. In this manner, the first slave laser 110-1 may measure the absorption/reflection of one feature while the master laser 105 may measure the absorption/reflection of another spectral feature without further adjustment.

The precision of the placement of the slave laser's emission may be greater than 1 MHz, even for laser emission whose spectral width is 10's of MHz. One scheme is to fit a Gaussian or appropriate line shape to the measured spectrum. Using line fitting techniques, it is possible to compute the center of the heterodyne signal, to a precision is many times smaller the width of the heterodyne signal. This computed center may become the feedback to control the slave laser 110 to a precision many times better than the width.

Acts 605–615 have explained how two discrete spectral features may be measured without the necessity of re-tuning a laser (thereby losing a spectral feature to which the laser was tuned). Optional acts 620 and 625 illustrate how a larger number of discrete measurements may be made. A second heterodyne signal may be generated by a second coupler 115 from, for example, output signals of the master laser 105 and a second slave laser 110-2 [act 620]. Similar to act 610, the second heterodyne signal may be converted into electrical form and delivered to the spectrum analyzer 130 for measurement. Using the measured frequency value of the second heterodyne signal, the second slave laser 110-2 may be tuned to a second offset, in this case relative to the master laser 105 [act 625].

In one implementation consistent with the principles of the invention, the second slave laser 110-2 may be tuned relative to the first slave laser 110-1, rather than the master laser 105. Such an implementation may be useful where the second heterodyne signal, if using the master laser 105, would exceed the bandwidth of the photodetector 120-2 (i.e., for a spectral feature that the photodetector is unable to reach in heterodyne frequency). In such an instance, the first slave laser 110-1 may be tuned to an intermediate point between the frequency of the master laser 105 and the desired spectral feature. The second slave laser 110-2 may be tuned relative to this intermediate point to reach the desired spectral feature.

Optional acts 620 and 625 may produce three discrete measurements of the sample volume 145 (i.e., by the master laser, the first slave laser 110-1, and the second slave laser 110-2). Similar tuning may be performed with additional slave lasers 110-3 to 110-n to produce a large number of discrete frequency/wavelength measurements without requiring that any of the lasers 105/110 be adjusted from their respective spectral locations [act 630]. Although these measurements may not be simultaneous, optical switch 135 may rapidly switch output signals from the various lasers 105/110 in succession to obtain an absorption data set that is nearly simultaneous [act 635]. Those skilled in the art will appreciate that simultaneous data may be obtained by adding other components (such as additional photodetectors 155) to the system 100.

Optional act 630 illustrates that continuous measurement values also may be obtained by (e.g., linearly) adjusting the wavelength of one or more slave lasers 110. For example, the first slave laser 110-1 may be initially tuned to a certain offset from the master laser 105 as described in acts 610 and 615. Then the first slave laser 110-1 may be adjusted (perhaps using the precise values from the spectrum analyzer 130) to obtain a continuous range of absorption data, for example, down one side of a spectral feature. Those skilled in the art will appreciate that acts 620-630 are scalable with additional components 110/115/120, and that they may be used to obtain both multiple discrete absorption measurements and continuous absorption measurements at fine resolution relative to a reference frequency/wavelength.

Figure 7A:
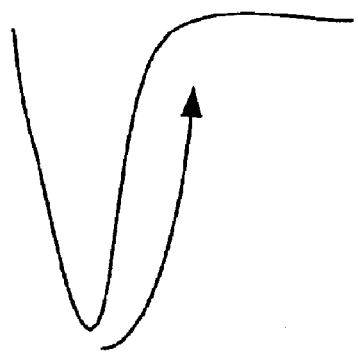
FIGS. 7A–7D are a number of spectral feature plots graphically illustrating various sampling techniques.
Figure 7B:
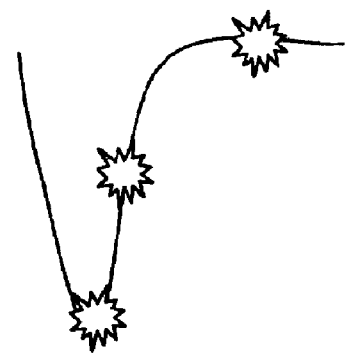

FIGS. 7A–7D are a number of spectral feature plots graphically illustrating various sampling techniques. FIG. 7A illustrates a typical method of a continuous scan of wavelength along a spectral feature. This continuous scan allows measurement of the complete line shape, but it takes a substantial time to acquire good statistics for each point. FIG. 7B is another typical scheme using 3 points: one on-line, side-line, and off-line. An advantage of such a scheme is speed, but a disadvantage of such a scheme is that the side-line (i.e., middle) point is constrained. The middle point may be constrained due to lack of precision in tuning a laser, or to difficulties present in derivative-tuning techniques.

Figure 7C:
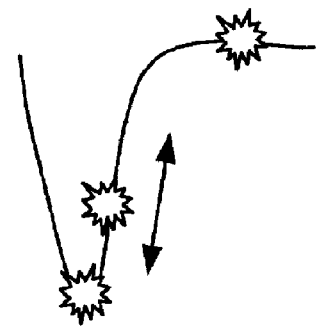
Figure 7D:
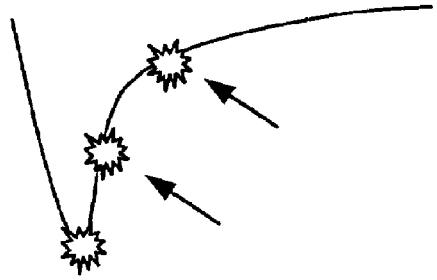

FIG. 7C illustrates an improvement, in an implementation consistent with the principles of the invention, over FIG. 7B in that the heterodyne master-slave arrangement described herein allows the side-line to be placed where needed for maximum measurement precision (e.g., adjustability shown by double arrows). The multiple-slave arrangement also allows for multiple side-lines. FIG. 7D illustrates how such a measurement may be optimized for remote sensing of, for example, total concentration in a sample column. Two or more measurements may be taken along the side-line where the column contains a wide range of densities and the user desires to resolve the contributions from various altitudes.

Conclusion

Systems and methods consistent with the present invention may use a spectrum analyzer to precisely measure an electrical signal obtained from a heterodyne signal from two laser sources. The spectrum analyzer enables precise measurement of frequency differences in the electrical signal, which may be used to precisely tune one laser source relative to the other. Such precisely tuned sources may be used for laser spectroscopy of a sample volume.

The foregoing description of exemplary embodiments of the present invention provides illustration and description, but is not intended to be exhaustive or to limit the invention to the precise form disclosed. Modifications and variations are possible in light of the above teachings or may be acquired from practice of the invention. For example, while certain components of the invention have been described as implemented in hardware and others in software, other hardware/software configurations may be possible. Also, while series of acts have been described with regard to FIGS. 5 and 6, the order of the acts is not critical.

Although the terms frequency and wavelength are used somewhat interchangeably herein, those skilled in the art will be able to readily convert between the two. It should be understood that while some precision values may be expressed in units of hertz (Hz), these frequency precision values may be converted to equivalent wavelength precision values (i.e., in units of meters (m) (e.g., picometers (pm)).

No element, act, or instruction used in the description of the present application should be construed as critical or essential to the invention unless explicitly described as such. Also, as used herein, the article "a" is intended to include one or more items. Where only one item is intended, the term "one" or similar language is used. The scope of the invention is defined by the following claims and their equivalents.

What is claimed is:

1. A method for adjusting a laser, comprising:

setting a first laser to output a first signal at a first wavelength;

combining the first signal and a second signal from a second laser to form a combined optical signal;

converting the combined optical signal to a combined electrical signal;

measuring the combined electrical signal to produce a precise measured value;

adjusting a second wavelength of the second signal relative to the first wavelength using the precise measured value;

sampling a volume containing material to be measured by inputting the first signal and the second signal into the volume; and detecting and measuring the first signal and the second signal after interaction with the material in the volume.

2. The method of claim 1, wherein the setting includes:

locking the first laser to a certain spectral feature.

3. The method of claim 1, wherein the precise measured value has a precision greater than 1 GHz.

4. The method of claim 1, wherein the precise measured value has a precision greater than 100 MHz.

5. The method of claim 1, wherein the precise measured value has a precision greater than 10 MHz.

6. The method of claim 1, further comprising:

combining the first signal and a third signal from a third laser to form another combined optical signal;

converting the another combined optical signal to another combined electrical signal;

measuring the another combined electrical signal to produce another precise measured value; and adjusting a wavelength of the third laser relative to the first wavelength using the another precise measured value.

7. The method of claim 6, further comprising:

detecting the first, second, and third signals after interaction with the material in the volume.

8. A system for tuning one or more second radiant sources relative to a first radiant source, comprising:

a coupler configured to combine output signals from the first radiant source and a second radiant source to generate a heterodyne signal containing a frequency difference between the output signals from the first radiant source and the second radiant source;

a photodetector configured to convert the heterodyne signal into an electrical signal containing the frequency difference;

spectrum analyzer configured to measure the frequency difference in the electrical signal and generate a precise difference value;

a controller configured to adjust a wavelength of the second radiant source relative to that of the first radiant source based on the precise difference value;

a sample volume containing a material to be measured, the sample volume being configured to receive the output signals from the first radiant source and the second radiant source; and another photodetector configured to measure the output signals from the first radiant source and the second radiant source after interaction with the sample volume.

9. The system of claim 8, further comprising:

an optical switch connected to the controller and configured to selectively supply the output signals from the first radiant source and the second radiant source to the sample volume.

10. The system of claim 8, further comprising:

a laser controller configured to vary at least one of a temperature and a current of the first radiant source and the second radiant source in response to control signals from the controller.

11. A system for tuning one or more second radiant sources relative to a first radiant source, comprising:

a coupler configured to combine output signals from the first radiant source and a second radiant source to generate a heterodyne signal containing a frequency difference between the output signals from the first radiant source and the second radiant source;

a photodetector configured to convert the heterodyne signal into an electrical signal containing the frequency difference;

a spectrum analyzer configured to measure the frequency difference in the electrical signal and generate a precise difference value;

a controller configured to adjust a wavelength of the second radiant source relative to that of the first radiant source based on the precise difference value;

a second coupler configured to combine output signals from the first radiant source and a third radiant source to generate a second heterodyne signal containing a second frequency difference between the output signals from the first radiant source and the third radiant source;

a second photodetector configured to convert the second heterodyne signal into a second electrical signal containing the second frequency difference; and a switch connected to the controller and configured to selectively apply the electrical signal and the second electrical signal to the spectrum analyzer.

12. The system of claim 8, wherein the spectrum analyzer is configured to generate the precise difference value with a precision greater than 10 MHz.

13. The system of claim 8, wherein the spectrum analyzer is configured to generate the precise difference value with a precision greater than 1 MHz.

14. The system of claim 8, wherein the spectrum analyzer is configured to generate the precise difference value with a precision greater than 100 kHz.

15. A system for tuning a second laser relative to a first laser, comprising:

a detector configured to produce an offset signal corresponding to a frequency difference between outputs of the first laser and the second laser;

a spectrum analyzer configured to measure a frequency of the offset signal and generate a precise measurement value;

a controller configured to tune the output of the second laser relative to the output of the first laser using the precise measurement value;

a sample volume containing a material to be measured, the sample volume configured to receive the output signals from the first laser and the second laser; and another detector configured to measure the output signals from the first laser and the second laser after interaction with the sample volume.

* * * * *